(12) United States Patent
Halamicek, III

(10) Patent No.: US 8,377,907 B1
(45) Date of Patent: Feb. 19, 2013

(54) COMPOSITIONS FOR TREATING ALCOHOL HANGOVER

(76) Inventor: William A. Halamicek, III, Aurora, CO (US)

( * ) Notice: Subject to any disclaimer, the term of this patent is extended or adjusted under 35 U.S.C. 154(b) by 156 days.

(21) Appl. No.: 13/031,413

(22) Filed: Feb. 21, 2011

(51) Int. Cl.
*A61K 31/685* (2006.01)
(52) U.S. Cl. ........................................................ 514/78
(58) Field of Classification Search ................ 514/78
See application file for complete search history.

(56) References Cited

U.S. PATENT DOCUMENTS

| | | | |
|---|---|---|---|
| 4,322,407 A * | 3/1982 | Ko | 424/601 |
| 4,496,548 A | 1/1985 | Moldowan | |
| 4,593,020 A | 6/1986 | Guinot | |
| 5,202,354 A | 4/1993 | Matsuoka | |
| 6,045,819 A | 4/2000 | Takebe | |
| 6,048,540 A | 4/2000 | Kim | |
| 6,517,831 B2 | 2/2003 | Takebe et al. | |
| 6,733,797 B1 * | 5/2004 | Summers | 424/728 |
| 6,913,769 B2 | 7/2005 | Oslick | |
| 7,063,865 B2 | 6/2006 | Jones et al. | |
| 2004/0162270 A1 | 8/2004 | Oslick | |
| 2005/0191386 A1 | 9/2005 | Adams | |
| 2005/0238710 A1 | 10/2005 | Connolly | |
| 2005/0271754 A1 | 12/2005 | Cochrane | |
| 2007/0196518 A1 | 8/2007 | Wojewnik | |
| 2007/0213400 A1 | 9/2007 | Okubo | |
| 2008/0020071 A1 | 1/2008 | Diaz | |
| 2008/0057110 A1 | 3/2008 | Skirpa | |
| 2008/0075710 A1 | 3/2008 | Cornett | |
| 2010/0048928 A1 | 2/2010 | Kato | |

\* cited by examiner

*Primary Examiner* — Elli Peselev
(74) *Attorney, Agent, or Firm* — Albert Haegele; Leyendecker & Lemire, LLC

(57) ABSTRACT

Compositions for treating alcohol hangover and methods of their use in treating or preventing hangover are described. The compositions include glycerophospholipids. Methods of use include administration or ingestion of the compositions after an episode of alcohol consumption. The compositions can be effective at preventing, eliminating, or reducing alcohol hangover when taken following an episode of alcohol consumption. In some embodiments, the glycerophospholipids are ingested with water or aqueous preparation, and some embodiments include B vitamins or other adjuvants.

7 Claims, No Drawings

COMPOSITIONS FOR TREATING ALCOHOL HANGOVER

BACKGROUND

Consumption of ethyl alcohol can result in a syndrome commonly referred to as "hangover" or "alcohol hangover." Alcohol hangover typically occurs several hours after alcohol consumption ceases, and includes physiological symptoms such as headache, lethargy, nausea, dehydration, insomnia, and general malaise. Alcohol hangovers vary greatly in severity, which correlates strongly with degree of alcohol intoxication preceding the alcohol hangover. Genetic variation can also affect alcohol hangover severity.

Alcohol hangovers typically occur after most, if not all, of the alcohol is cleared from a drinker's body. The drinker may have slept for several hours as well. Accordingly, alcohol hangover generally does not occur during acute alcohol intoxication. Clearance of alcohol from a drinker's body is typically achieved primarily through metabolism of alcohol to acetaldehyde, which is subsequently metabolized to acetic acid, and then to carbon dioxide. Some alcohol is also excreted unchanged.

Many putative alcohol hangover remedies are known. Most are relatively ineffective and some are potentially dangerous. For instance, treatment of alcohol hangover with acetaminophen, which can be effective at reducing headache, can cause liver damage or exacerbate liver damage caused by alcohol or acetaldehyde. Treatments that have been shown to reduce some alcohol hangover symptoms include water or beverage consumption, food consumption, administration of B vitamins, administration of coffee or other caffeine sources, and administration of non-steroidal anti-inflammatory drugs (NSAIDs. However, most alcohol hangover treatments are relatively ineffective at mitigation of severe alcohol hangover symptoms.

DETAILED DESCRIPTION

Embodiments of the present invention comprise compositions or methods for treating alcohol hangover. The compositions or methods include one or more glycerophospholipids or administration thereof. Variations of the one or more glycerophospholipids are extracted from or contained in lecithin.

Embodiments of the present invention include one or more of the following ingredients for administration concurrently with glycerophospholipids: water, citrate, ascorbate (vitamin C), glutathione, N-acetyl cysteine, thiamine (vitamin B1, riboflavin (Vitamin B2), niacin or nicotinamide (Vitamin B3, pantothenate (Vitamin B5), pyridoxine (Vitamin B6), folate (Vitamin B9), cyanocobalamin (Vitamin B12), biotin (Vitamin B7), trimethylglycine, choline, inositol, and para-aminobenzoic acid.

In some embodiments, glycerophospholipids for preventing or treating alcohol hangover include: phosphatidic acid (PA), phosphatidylcholine (PC), phosphatidylethanolamine (PE), phosphatidylinositol (PI), or phosphatidylserine (PS). The glycerophospholipids can be constituents of or derived from lecithin, including, but not limited to, lecithin from animal or vegetable sources. Animal sources of lecithin include poultry eggs, and vegetable sources include vegetable oils such as soy oil. In some embodiments the glycerophospholipids are separated from lecithin through super critical fluid extraction, resulting in a composition that is about 95% glycerophospholipids by weight.

Embodiments of compositions for treatment of alcohol hangover are typically, but not necessarily, administered after an episode of alcohol consumption has ceased. Compositions are typically most effective when administered after an episode of drinking has ceased but before the drinker retires for sleep. However, compositions administered after the drinker awakens from sleep are also effective at mitigating alcohol hangover. In some variations, the compositions are administered both before the drinker retires for sleep and after he or she awakens therefrom. While compositions according to the present invention can be administered before cessation of an episode of drinking, the glycerophospholipids are not thought to substantially modulate alcohol clearance or metabolism, or otherwise alter acute alcohol effects.

In some embodiments, the glycerophospholipids are administered concurrently with water or aqueous preparation. Drinking water can help mitigate alcohol induced dehydration, which typically contributes to alcohol hangover. In some embodiments, the aqueous preparation includes citrate, which can enhance water absorption. The citrate can be in isotonic, hypotonic, or hypertonic solution in water.

Hangover treatment by ingestion of compositions for treatment of alcohol hangover commences preferably within 18 hours after substantial alcohol consumption, more preferably approximately 0-5 hours after substantial alcohol consumption, and most preferably after substantial alcohol consumption and approximately 0-1.5 hours after ceasing alcohol consumption. Substantial alcohol consumption includes consuming at least 1.2 ounces of alcohol in less than two hours.

TERMINOLOGY

The terms and phrases as indicated in quotation marks ("") in this section are intended to have the meaning ascribed to them in this Terminology section applied to them throughout this document, including in the claims, unless clearly indicated otherwise in context. Further, as applicable, the stated definitions are to apply, regardless of the word or phrase's case, to the singular and plural variations of the defined word or phrase.

The term "or" as used in this specification and the appended claims is not meant to be exclusive; rather the term is inclusive, meaning either or both.

References in the specification to "one embodiment", "an embodiment", "another embodiment", "a preferred embodiment", "an alternative embodiment", "one variation", "a variation" and similar phrases mean that a particular feature, structure, or characteristic described in connection with the embodiment or variation, is included in at least an embodiment or variation of the invention. The phrase "in one embodiment", "in one variation" or similar phrases, as used in various places in the specification, are not necessarily meant to refer to the same embodiment or the same variation.

The term "approximately," as used in this specification and appended claims, refers to plus or minus 10% of the value given.

The term "about," as used in this specification and appended claims, refers to plus or minus 20% of the value given.

The terms "generally" and "substantially," as used in this specification and appended claims, mean mostly, or for the most part.

The term "alcohol," as used in this specification and appended claims, refers to ethyl alcohol.

The terms "ingest," "ingesting," "administration," and similar terms, as used in this specification and appended claims, refers to taking a composition into one's body over a time interval of less than 60 minutes. Ingestion includes oral and parenteral administration. Ingestion is typically, but not necessarily, by oral administration.

The term "serving," as used in this specification and appended claims, refers to a quantity of material ingested, administered, or recommended to be ingested or administered, within a time interval of less than 60 minutes. For example, a dry powder preparation of 95% by weight glycerophospholipid packaged in bulk in an amount of 242 grams contains 500 servings where a serving size is 460 mg glycerophospholipid. In another example, for a preparation of 95% by weight glycerophospholipid encapsulated in aliquots of 242 mg per capsule, a serving is two capsules where a serving size is 460 mg glycerophospholipid. A serving can be considered a "dose" for the purposes of this specification and appended claims.

The terms "treating hangover," "hangover treatment," "treatment of alcohol hangover," and similar terms, as used in this specification and appended claims, refer to ingestion or administration of a composition of matter directed to prevention or mitigation of alcohol hangover symptoms.

The term "blend," as used in this specification and appended claims, refers to an intermingled combination of components such as a suspension, emulsion, solution, or mixture.

The term "thiamin HCl," as used in this specification and appended claims, refers to the hydrochloride salt of thiamin, or to other thiamin containing compounds. Where a quantity of thiamin HCl is specified, a quantity of compound having an equivalent amount of thiamin is considered the same as the specified quantity of thiamin HCl. For example, where 125 mg thiamin HCl (molecular weight=337) is specified, 157 mg of thiamin pyrophosphate (molecular weight=424) is considered the same as 125 mg thiamin HCl.

The term "niacin," as used in this specification and appended claims, refers to nicotinic acid or other compounds having vitamin B3 activity, such as but not limited to nicotinamide, other amide derivatives of nicotinic acid, and nicotinic acid esters. Where a quantity of niacin is specified, a quantity of compound having an equivalent amount of vitamin B3 activity is considered the same as the specified quantity of niacin.

The term "calcium pantothenate," as used in this specification and appended claims, refers to a calcium salt of pantothenic acid, or other compounds having vitamin B5 activity, including, but not limited to pantothenic acid and pantothenol. Where a quantity of calcium pantothenate is specified, a quantity of compound having an equivalent amount of vitamin B5 activity is considered the same as the specified quantity of calcium pantothenate.

The term "pyridoxine HCl," as used in this specification and appended claims, refers to the hydrochloride salt of pyridoxine, or to other compounds having vitamin B6 activity, including, but not limited to, pyridoxal, pyridoxine phosphate, and 4-pyridoxic acid. Where a quantity of pyridoxine HCl is specified, a quantity of compound having an equivalent amount of vitamin B6 activity is considered the same as the specified quantity of pyridoxine HCl.

The term "cyanocobalamin," as used in this specification and appended claims, refers to any cobalamin compound having vitamin B12 activity in humans, including but not limited to hydroxocobalamin and methylcobalamin. Where a quantity of cyanocobalamin is specified, a quantity of compound having an equivalent amount of vitamin B12 activity is considered the same as the specified quantity of cyanocobalamin.

The term "folate," as used in this specification and appended claims, refers to the folate anion or any compound having vitamin B9 activity. Where a quantity of folate is specified, a quantity of compound having an equivalent amount of vitamin B9 activity is considered the same as the specified quantity of folate. The same principle applied to the B vitamins described above is applicable to ascorbate and choline as well. An ascorbate ester is considered equivalent to ascorbate, and where a quantity of ascorbate is specified, a quantity of compound having an equivalent amount of vitamin C activity is considered the same as the specified quantity of ascorbate. Similarly, where a quantity of choline bitartrate is specified, a quantity of compound having an equivalent amount of choline is considered the same as the specified quantity of choline bitartrate.

A First Embodiment Composition for Treating Alcohol Hangover

A first embodiment composition for treating alcohol hangover comprises a powder or granular solid including approximately 95% by weight glycerophospholipid. The composition includes glycerophospholipid in an amount of preferably at least 460 mg per serving, more preferably at least 920 mg per serving, still more preferably at least 1380 mg per serving, and most preferably at least 2300 mg per serving. The glycerophospholipid of the first embodiment is derived from soy lecithin and includes approximately 24.2% by weight PC, 21.1% by weight PE, and 14.7% by weight PI.

The composition is typically, but not necessarily, ingested in capsules or as a blend in water or aqueous solution.

A Second Embodiment Composition for Treating Alcohol Hangover

A second embodiment composition for treating alcohol hangover comprises a blend of 800 mg to 1400 mg PC and approximately 500 mg to 875 mg PI in 150 mL to 450 mL of approximately 39 mM aqueous citrate sweetened with aspartame. Variations included aqueous citrate in a concentration range of preferably 0-133 mM citrate, more preferably 5 mM-78 mM citrate, and most preferably about 39 mM citrate.

The blend of the second embodiment composition further comprises:
  500 mg ascorbate;
  250 mg glutathione;
  600 mg N-acetyl cysteine;
  100 mg vitamin B1; (as thiamin HCl)
  50 mg vitamin B2; (riboflavin)
  200 mg vitamin B3; (as niacinamide and niacin)
  75 mg vitamin B6; (as pyridoxine HCl)
  800 µg folate;
  1 mg vitamin B12; (as cyanocobalamin)
  600 ug biotin;
  1000 mg pantothenate; (as D-calcium pantothenate)
  50 mg trimethylglycine;
  45 mg choline; (as choline bitartrate)
  250 mg inositol; and
  100 mg para-aminobenzoic acid.

A First Method of Treating Alcohol Hangover

A first method of treating hangover comprises orally ingesting a first serving of the first embodiment composition for treating alcohol hangover, the first serving having a mass of approximately 6 grams, which includes approximately 5.7 grams glycerophospholipid. Within 18 hours of consuming at least 1.2 ounces of alcohol, the first serving is combined and ingested with about 350 mL of approximately 39 mM aqueous citrate sweetened with a small amount of aspartame.

A Second Method of Treating Alcohol Hangover

A second method of treating hangover comprises orally ingesting a second serving of the first embodiment composition for treating alcohol hangover, the second serving having a mass of approximately 4 grams distributed about evenly among at least 4 capsules. The second serving consists essentially of approximately 3.8 grams glycerophospholipid. Within 18 hours of consuming at lest 1.2 ounces alcohol, the 4 capsules are ingested with about 232 mL water A Third Method of Treating Alcohol Hangover A third method of treating alcohol hangover comprises orally ingesting a third serving of the first embodiment composition for treating hangover, the third serving having a mass of approximately 2 grams distributed among at least 2 capsules. The second serving consists essentially of approximately 1.9 grams glycerophospholipid. The capsules are swallowed with about 116 mL water. The third serving is ingested within 18 hours after consuming at least 1.2 ounces of alcohol.

A Fourth Method of Treating Alcohol Hangover

A fourth method of treating alcohol hangover comprises ingesting the second embodiment composition for treating hangover, said ingesting occurring within 18 hours of consuming at least 1.2 ounces of alcohol.

EXAMPLES OF TREATING ALCOHOL HANGOVER

Example 1

A 23 year old male subject weighing approximately 175 pounds consumed approximately 7.8 ounces of alcohol (about 15 ounces of 80 proof tequila and 36 ounces of beer) over a time interval of approximately 5.5 hours. During the 5.5 hour interval, at not time did the subject consume less than about 1 ounce alcohol per hour. The subject lapsed into semiconsciousness within 30 minutes of consuming his last alcoholic beverage. About an hour later the subject performed the fourth method of treating alcohol hangover, which included ingesting approximately 1150 mg PC and approximately 700 mg PI suspended in approximately 280 mL 0.39 mM aqueous citrate.

After about 9 hours sleep, the subject reported feeling well, with alcohol hangover symptoms being minimal.

Example 2

A 21 year old male subject weighing approximately 160 pounds consumed approximately 7.8 ounces of alcohol (about 15 ounces of 80 proof tequila and 36 ounces of beer) over a time interval of approximately 5.5 hours. During the 5.5 hour interval, at not time did the subject consume less than about 1 ounce alcohol per hour. The subject performed the fourth method of treating alcohol hangover before retiring for the evening, the fourth method including ingesting approximately 1150 mg PC and approximately 700 mg PI with approximately 375 mL 0.39 mM aqueous citrate.

After about 7.5 hours sleep, the subject reported a complete absence of alcohol hangover.

Example 3

A 45 year old male subject, weight unknown, displayed symptoms of moderate to severe alcohol intoxication after consuming an unknown amount of alcohol. The subject performed the fourth method of treating alcohol hangover before retiring for the evening, the fourth method including ingesting approximately 1150 mg PC and approximately 700 mg PI with approximately 375 mL 0.39 mM aqueous citrate.

After about 8 hours sleep, the subject reported a complete absence of alcohol hangover.

Example 4

A 55 year old male subject reported awakening with moderate alcohol hangover the morning after consuming an unknown amount of alcohol. Within two hours of awakening with the moderate alcohol hangover, the subject performed the fourth method of treating alcohol hangover, the fourth method including ingesting approximately 1150 mg PC and approximately 700 mg PI with approximately 440 mL 0.39 mM aqueous citrate.

The subject reported that alcohol hangover abated promptly after performing the fourth method of treating hangover, with hangover symptoms almost completely absent after an hour.

Example 5

A 45 year old male subject displayed severe alcohol hangover, including severe malaise, headache, nausea, and vomiting, the morning after consuming an unknown amount of alcohol. The subject reported "heavy" alcohol consumption the night before. After reporting severe alcohol hangover, the subject performed the fourth method of treating alcohol hangover, the fourth method including ingesting approximately 1150 mg PC and approximately 700 mg PI with approximately 440 mL 0.39 mM aqueous citrate.

About 90 minutes after performing the fourth method of treating hangover, the subject reported feeling "much better," with headache and nausea completely absent. The subject ingested no analgesics or NSAIDs.

Example 6

A 53 year old male subject weighing approximately 180 pounds consumed about 2.4 ounces of alcohol over a time interval of about 3 hours. The subject reported that episodes of alcohol consumption almost always induced sleep disturbances characterized by frequent awakening during the night subsequent to the alcohol consumption. Approximately 2 hours after ceasing alcohol consumption, the subject performed the second method of treating hangover before retiring for the evening. The second method includes ingesting approximately 3.8 grams glycerophospholipid with about 232 mL water, the glycerophospholipid including approximately 24.2% by weight PC, 21.1% by weight PE, and 14.7% by weight PI.

The subject reported sleeping relatively soundly after the second treatment, with the usual alcohol induced sleep disturbances being absent.

Example 7

A 36 year old female, weight unknown, reported consuming approximately 6 ounces of alcohol (approximately ten servings of beer and 3 shots of 80 proof liquor) over a time interval of about 4.5 hours. The subject performed the fourth method of treating hangover after ceasing alcohol consumption and before retiring. The fourth method of treating hangover included ingesting approximately 800 mg PC and 500 mg PI in 150 ml 0.39 mM aqueous citrate.

The subject reported feeling "fine" the following morning, with alcohol hangover symptoms largely absent.

Example 8

A 43 year old female subject reported experiencing hangover symptoms including severe malaise, headache, and nausea, the morning after a night of "heavy drinking." The amount of alcohol consumed during the night of heavy drinking is unknown. The subject was bedridden as a result of the hangover prior to performing the fourth method of treating hangover, the fourth method including ingesting approximately 1150 mg PC and approximately 700 mg PI with approximately 440 mL 0.39 mM aqueous citrate.

About 3 hours after performing the fourth method, the subject was able to perform "normal activities," with alcohol hangover symptoms greatly reduced.

Alternative Embodiments and Variations

The various embodiments and variations thereof, illustrated in the accompanying Figures and/or described above, are merely exemplary and are not meant to limit the scope of the invention. It is to be appreciated that numerous other variations of the invention have been contemplated, as would be obvious to one of ordinary skill in the art, given the benefit of this disclosure. All variations of the invention that read upon appended claims are intended and contemplated to be within the scope of the invention.

I claim:

1. A composition for treating alcohol hangover comprising:
   at least 1100 mg glycerophospholipid per serving, the glycerophospholipid (i) being selected from the group consisting of phosphatidic acid, phosphatidylcholine, phosphatidylethanolamine, phosphatidylinositol, and phosphatidylserine and (ii) including at least 800 mg phosphatidylcholine;
   at least twelve ounces of water per serving;
   water soluble electrolytes at a total electrolyte ionic strength of less than 175 mEq/L, the water soluble electrolytes including citrate dissolved in the water at a concentration of at least 5 mM;
   at least 125 mg ascorbate per serving;
   at least 125 mg glutathione per serving;
   at least 300 mg N-acetyl cysteine per serving;
   at least 100 mg thiamin HCl per serving;
   at least 50 mg Riboflavin per serving;
   at least 100 mg vitamin B3 per serving;
   at least 37.5 mg pyridoxine HCl per serving;
   at least 800 µg folate per serving;
   at least 500 µg cyanocobalamin per serving;
   at least 300 ug biotin per serving;
   at least 500 mg D-calcium pantothenate per serving;
   at least 25 mg trimethylglycine per serving;
   at least 22.5 mg choline bitartrate per serving;
   at least 125 mg inositol per serving; and
   at least 50 mg para-aminobenzoic acid per serving.

2. A method of treating alcohol hangover comprising ingesting one or more servings of a composition, the composition including at least 460 mg glycerophospholipid per serving.

3. The method of treating alcohol hangover of claim 2, wherein:
   the at least 460 mg glycerophospholipid comprises at least 1100 mg glycerophospholipid;
   the glycerophospholipid is selected from the group consisting of phosphatide acid, phosphatidylcholine, phosphatidylethanolamine, phosphatidylinositol, and phosphatidylserine; and
   the glycerophospholipid includes at least 400 mg phosphatidylcholine and at least 200 mg phosphatidylinositol.

4. The method of treating alcohol hangover of claim 3, wherein:
   the composition further comprises water soluble electrolytes and at least eight ounces of water per serving, the water soluble electrolytes including citrate dissolved in the water at a concentration of at least 5 mM; and
   the glycerophospholipid further includes at least 800 mg phosphatidylcholine.

5. A method of treating alcohol hangover comprising ingesting one or more servings of a composition, the composition including (i) at least 1100 mg glycerophospholipid per serving, the glycerophospholipid including at least 400 mg phosphatidylcholine and at least 200 mg phosphatidylinositol, and (ii) at least eight ounces of 5 mM or greater aqueous citrate per serving.

6. A composition for treating alcohol hangover comprising:
   at least 1100 mg glycerophospholipid per serving, the glycerophospholipid including at least 400 mg phosphatidylcholine and at least 200 mg phosphatidylinositol;
   at least twelve ounces of 5 mM or greater aqueous citrate per serving;
   at least 125 mg ascorbate per serving;
   at least 125 mg glutathione per serving;
   at least 300 mg N-acetyl cysteine per serving;
   at least 100 mg thiamin HCl per serving;
   at least 50 mg Riboflavin per serving;
   at least 100 mg vitamin B3 per serving;
   at least 37.5 mg pyridoxine HCl per serving;
   at least 800 µg folate per serving;
   at least 500 µg cyanocobalamin per serving;
   at least 300 ug biotin per serving;
   at least 500 mg D-calcium pantothenate per serving;
   at least 25 mg trimethylglycine per serving;
   at least 22.5 mg choline bitartrate per serving;
   at least 125 mg inositol per serving; and
   at least 50 mg para-aminobenzoic acid per serving.

7. A method of treating alcohol hangover comprising ingesting one or more servings of the composition of claim 6.

* * * * *